US008808668B2

(12) United States Patent
Poelzing et al.

(10) Patent No.: US 8,808,668 B2
(45) Date of Patent: Aug. 19, 2014

(54) X-RAY ATTENUATING COMPOSITIONS AND METHODS

(75) Inventors: Steven Poelzing, Salt Lake City, UT (US); Rengasayee Veeraraghavan, Salt Lake City, UT (US); Adam Smoot, Bountiful, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1174 days.

(21) Appl. No.: 12/423,618

(22) Filed: Apr. 14, 2009

(65) Prior Publication Data

US 2009/0266995 A1 Oct. 29, 2009

Related U.S. Application Data

(60) Provisional application No. 61/044,786, filed on Apr. 14, 2008.

(51) Int. Cl.
*A61K 49/04* (2006.01)
*A61B 5/055* (2006.01)
*G01N 23/223* (2006.01)

(52) U.S. Cl.
CPC .................. *A61K 49/0433* (2013.01)
USPC .......... 424/9.45; 600/407; 600/425; 600/427; 600/428; 600/429; 378/46; 424/9.4

(58) Field of Classification Search
USPC .......... 424/9.4, 9.45; 600/407, 425, 426, 427, 600/428, 429; 378/46
See application file for complete search history.

(56) References Cited

U.S. PATENT DOCUMENTS 7,790,141 B2 * 9/2010 Pathak et al. ................ 424/1.89

OTHER PUBLICATIONS

Guirado et al.; Understanding Electrochromic Processes Initiated by Dithienylcyclopentene Cation-Radicals; J. Phys. Chem. B.; 2005; pp. 17445-17459; vol. 109.
Shrimpton, P.C., Electron density values of various human tissues: in vitro Compton scatter measurements and calculated ranges, Phys. Med. Biol., 1981, vol. 26. No. 5, pp. 907-911.
Blackwell, David D., et al., Antenna impedance measurement in a magnetized plasma. II. Dipole antenna., Physics of Plasmas 14, 092106 (2007); pp. 1-8.
Brady, G.W., et al., Structure Studies of Solutions of Large Organic Molecules. I. C9H19I and C18H36I2 in Decalin., J Chem Phys 1969, vol. 51, No. 10, pp. 4309-4319.
Harada, Makoto, et al., Hydration Structures of Bromides on Cationic Micelles, J Phys Chem B 2007, 111, pp. 12136-12140.
Hoge, Richard D., et al., Oxidative metabolism and the detection of neuronal activation via imaging, J Chem Neuroanatomy 22 (2001), pp. 43-52.
Kobrinsky, Evgeny, et al., Voltage-gated Mobility of the Ca2+ Channel Cytoplasmic Tails and its Regulatory Role, J Biol Chem 2002, M211254200.
Logothetis, Nikos K., et al., Neurophysiological investigation of the basis of the fMRI signal, Nature, vol. 412, 2001, pp. 150-157.
Nikki, Kunio, et al., Remarkable changes in conformations of n-alkanes with their carbon numbers and aromatic solvents, Royal Society of Chem., 2001, pp. 2370-2373.
Sakane, Hideto, et al., XAFS analysis of triiodide ion in solutions, Journal of Synchrotron Radiation, 2001, 8, pp. 674-676.
Stabin, Michael G., et al., Voxel-Based Mouse and Rat Models for Internal Dose Calculations, . J Nucl Med, 2006, 47, pp. 655-659.
Taccardi, Bruno, et al., Useful Lessons from Body Surface Mapping, J Cardiovasc Electrophysiol, vol. 9, 1998, pp. 773-786.
Wang, Yong, et al., Application of the Method of Fundamental Solutions to Potential-based Inverse Electrocardiography, Ann Biomed Eng. 2006,34(8), pp. 1272-1288.
Xie, Yong, et al., Transmission of light through slit apertures in metallic films, Optical Society of America, 2004.
Baxter, William T., et al., Visualizing Excitation Waves inside Cardiac Muscle Using Transillumination, Biophysical Journal, vol. 80, 2001, pp. 516-530.
Poelzing, Steven, et al., Novel x-ray attenuation mechanism: Role of interatomic distance, Med Phys 35 (10), 2008, pp. 4386-4395.

* cited by examiner

*Primary Examiner* — Michael G Hartley
*Assistant Examiner* — Leah Schlientz
(74) *Attorney, Agent, or Firm* — Thorpe North & Western LLP (57) ABSTRACT

The present invention provides methods and compositions for modulating x-ray attenuation, where the x-ray attenuation compound can comprise a molecule having at least two conformational states, a first k-edge atom attached to the molecule at a first position, and a second k-edge atom attached to the molecule at a second position, where the molecule changes from a first conformational state to a second conformational state in response to an external stimulus. Additionally, a first interatom distance between the first k-edge atom and the second k-edge atom in the first conformational state can be within a first harmonic error of 0 to about 0.2, and a second interatom distance between the first k-edge atom and the second k-edge atom in the second conformational state can be within a second harmonic error of about 0.8 to 1.0.

12 Claims, 7 Drawing Sheets

X-RAY ATTENUATING COMPOSITIONS AND METHODS

RELATED APPLICATION

This application claims the benefit of U.S. Provisional Application No. 61/044,786, filed Apr. 14, 2008, which is incorporated herein by reference.

BACKGROUND OF THE INVENTION

Less than a year after Roentgen's demonstration of x-ray based imaging, two groups reproduced his findings and also proposed the use of x-ray contrast enhancing media allowing for greater differentiation between soft tissues and blood vessels. Since then, these contrast enhancing media, or "contrast agents," have evolved over the past century to the current state of well tolerated and highly efficacious drugs used in the vast majority of patient CT examinations. The past half century has mainly focused on the development of agents with limited bio-toxicity and in some respects on agents that can provide enhancement of specific anatomical markers such as blood vessels and plaques.

The quantification of physiology however, has been principally the purview of other imaging modalities such as contrast enhanced glucose uptake quantified by positron emission tomography or MRI measurements of oxygen consumption. The choice of imaging modality has much to do with the risk to the patient, the unique physics associated with photon-mass interactions, radioactive decay, and nuclear spin. Additionally, the unique physics of each modality can yield relatively specific physiological insights.

However, three-dimensional imaging modalities have been unable to non-invasively and directly measure electrical activity inherent in many cell types including neural, cardiac, and skeletal muscle tissue. Instead, the electroencephalograph (EEG), electrocardiograph (ECG), and electromyograph (EMG) have received the majority of focus for measurement of electrical phenomena. All of these techniques are limited to a two-dimensional surface and rely on significant anatomical and morphological assumptions for "inverse problem" reconstruction of subdermal electrical activity. Even after all the assumptions are implemented, the reconstructed potentials are again fit to a surface and cannot yield significant information about the electrical activity within deeper layers of muscular or neurological tissue.

Likewise, previous imaging modalities have been unable to measure intracellular ion concentrations non-invasively and in-vivo. Again the limitation here is that there are no effective agents capable of transducing these biological parameters into a signal useful for three-dimensional reconstruction. One mechanism for imaging electrical activity, and thereby potentially even ionic concentrations, in three-dimensions has been demonstrated in isolated whole-heart preparations using voltage sensitive dyes. Briefly, a piece of muscular tissue is illuminated from both sides (transillumination), and a dye capable of changing its fluorescence properties in response to a change in membrane potential, is mapped with high temporal and spatial resolution cameras from either side of the heart. Mathematical assumptions are again employed to reconstruct activity within the wall of the heart. This technique however is unlikely to be employed in the body because voltage sensitive optical dyes emit and absorb ultraviolet through infrared excitation light sources, a light spectrum of energy insufficient for imaging deeper than a few millimeters to a centimeter.

As such, imaging modality for transducing biological phenomena in three-dimensions and other measuring techniques for biological phenomena, such as membrane potential or intracellular ionic concentrations, as well as other properties, continue to be sought.

BRIEF DESCRIPTION OF THE DRAWINGS

FIGS. 4A and 4B shows diiodomethane absorbs significantly more than twice the concentration of iodomethane.

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, the singular forms "a," "an," and "the" include plural referents unless the context clearly dictates otherwise. Thus, for example, reference to "a conformational group" includes one or more of such groups, reference to "a k-edge atom" includes reference to one or more of such atoms, and reference to the step of "applying an electrical field" includes reference to one or more of such steps.

Definitions

In describing and claiming the present invention, the following terminology will be used in accordance with the definitions set forth below.

As used herein, "attenuation" refers to an ability of a compound to change an energy source through chemical and/or physical phenomenon, e.g., absorption or scattering. This term includes x-ray attenuation and UV absorption and fluorescence.

As used herein, "tissue" refers to any biological tissue including, but not limited to, epithelium, connective, muscle, organ, bone, and nervous tissues.

As used herein, "harmonic error" ($E_H$) refers to the fractional remainder of the inter-atom distance (d) and the wavelength of the photon necessary for K-shell photoelectric attenuation ($\lambda_K$). For iodine, the interatom distance is $d_{I,I}$ and the wavelength for K-shell photoelectric attenuation ($\lambda_{K,I}$) is 0.375 Å.

$$E_H = \frac{d_{I,I}}{\lambda_{K,I}} - \left\lfloor \frac{d_{I,I}}{\lambda_{K,I}} \right\rfloor$$

where $\lfloor \rfloor$ is the floor function. $E_H$ is bounded from 0 to 1 for all elements. Measurable x-ray attenuation differences can vary depending on the equipment used, however most current equipment can distinguish an absolute difference between the harmonic errors of the first state and second state of 0.2 or greater. The distance between the first k-edge atom and the second k-edge atom in any molecular conformational state can be within a harmonic error of 0 to 1.

As used herein, "conformational state" refers to one of at least two stable or metastable spatial configurations of a molecule which may be preferred or less preferred in response to an external stimulus or stimuli, or lack thereof.

As used herein, the term "substantially" or "substantial" refers to the complete or nearly complete extent or degree of an action, characteristic, property, state, structure, item, or result. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" a component would either completely lack such component, or so nearly completely lack such that the relevant effect would be the same as if it completely lacked the same.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 10 to about 50" should be interpreted to include not only the explicitly recited values of about 10 to about 50, but also include individual values and sub-ranges within the indicated range. Thus, included in this numerical range are individual values such as 20, 30, and 40 and sub-ranges such as from 10-30, from 20-40, and from 30-50, etc. This same principle applies to ranges reciting only one numerical value. Furthermore, such an interpretation should apply regardless of the breadth of the range or the characteristics being described. The term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. Consistent with the above concept, the term "about" also includes "exactly" without effect on any degree of equivalence to the same, unless specifically stated otherwise.

In the present disclosure, the term "preferably" or "preferred" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

It has been recognized that it would be advantageous to develop an x-ray attenuating compound that is able to measure x-ray attenuation in response to various external stimuli including biological stimuli. Accordingly, the absorbance of a polychromatic x-ray beam can be modulated by the distance between covalently linked strong x-ray attenuating atoms like iodine. In specific, x-ray absorbance is lowest when the inter-iodine nuclear distance is closest to a harmonic of the energy required for photoelectric absorbance by the inner most electron orbital (K-shell). X-ray absorbance increases as the fractional distance between iodine atoms, relative to the photon wavelength necessary for K-shell absorbance, increases.

An x-ray attenuating compound can comprise a molecule having at least two conformational states, a first k-edge atom attached to the molecule at a first position, and a second k-edge atom attached to the molecule at a second position, where the molecule changes from a first conformational state to a second conformational state in response to an external stimulus. Additionally, a first interatom distance between the first k-edge atom and the second k-edge atom in the first conformational state can be within a first harmonic error having a remainder of 0 to about 0.2, and a second interatom distance between the first k-edge atom and the second k-edge atom in the second conformational state can be within a second harmonic error with a remainder of about 0.8 to 0.99.

The molecule can be an organic molecule. Additionally, the organic molecule can be a substituted or unsubstituted, aliphatic and/or aromatic, carbon molecule. The first k-edge atom and/or the second k-edge atom can be a member selected from the group consisting of iodine, cesium, barium, lanthanum, gadolinium, tantalum, tungsten, and gold. As such, in one embodiment, the first k-edge atom and the second k-edge atom are the same element, such as iodine.

The first harmonic error can be 0 to about 0.2, although values outside this range may be suitable. In one specific aspect, the first harmonic error can be about 0. Additionally, the second harmonic error can be about 0.8 to 0.99. In one specific aspect, the second harmonic error can be about 0.99.

The external stimulus can include various stimuli such as temperature, voltage, chemical, and/or compounds, including biological compounds.

Additionally, the x-ray attenuating compound can further comprise a third k-edge atom and a fourth k-edge atom. Without being bound to any particular theory, it is thought that a weighted average of the harmonic error between all k-edge atoms can be different from the weighted average of the harmonic errors between all k-edge atoms in any other conformational state by a minimum detectable limit, e.g. 0.2. A third interatom distance between the third k-edge atom and the fourth k-edge atom in the first conformational can be within a third harmonic error of within about 0.2 of 0 or 1, and wherein a fourth interatom distance between the third k-edge atom and the fourth k-edge atom in the second conformational state can be within a fourth harmonic error of within about 0.2 of 0 or 1. The third k-edge atom and/or fourth k-edge atom can be independently selected from the group consisting of iodine, cesium, barium, lanthanum, gadolinium, tantalum, tungsten, and gold. In one specific example, the third k-edge atom and the fourth k-edge atom are gadolinium.

For more than two Iodine atoms, for example, it could be that the harmonic error (HE) of two iodine atoms would disproportionately influence attenuation relative to any other comparison of two atoms. The equations below show a hypothetical molecule with two conformational states. There are three harmonic errors associated with the three iodine atoms. The first number is the inter-iodine distance in angstroms. An average of the harmonic errors may be used in some embodiments. The relationship then for 4 atoms can have this same complexity.

A method of enhancing x-ray attenuation of an x-ray attenuating compound can include choosing a molecule capable of modulating from a first conformational state to a second conformational state in response to an external stimulus, determining a first interatom distance between a first k-edge atom and a second k-edge atom in the first conformational state within a first harmonic error having a remainder of 0 to about 0.2, determining a second interatom distance between the first k-edge atom and the second k-edge atom in the second conformational state within a second harmonic error with a remainder of about 0.8 to 1.0, attaching the first k-edge atom to the molecule at a first position, and attaching the second k-edge atom to the molecule at a second position, such that the first position and the second position provide the first interatom distance in the first conformational state and the second interatom distance in the second conformational state.

A third interatom distance can be determined between a third k-edge atom and a fourth k-edge atom in the first conformational state within a third harmonic error of within about 0.2 of 0 or 1, while a fourth interatom distance can be determined between the third k-edge atom and the fourth k-edge atom in the second conformational state within a fourth harmonic error of within about 0.2 of 0 or 1. A third k-edge atom can be attached to the molecule at a third position, and a fourth k-edge atom can be attached to the molecule at a fourth position, such that the third position and the fourth position provide the third interatom distance in the first conformational state and the fourth interatom distance in the second conformational state.

Additionally, a method of measuring x-ray attenuation of a sample with an x-ray attenuating compound as previously described can comprise the steps of adding the x-ray attenuating compound to the sample, the sample having the external stimulus in an amount sufficient to modulate the x-ray attenuating compound from the first conformational state to the second conformational state; exposing the x-ray attenuating compound to an energy source; and calculating the amount of the external stimulus present in the sample by measuring a difference in x-ray attenuation of the energy source provided by the first conformational state and the second conformational state of the x-ray attenuating molecule.

The method can further include the steps of collecting data of the external stimulus and imaging the data. Additionally, such steps can be dynamic. In one aspect, the method can be used in conjunction with computed tomography (CT) instrumentation to provide time-elapsed imagery of the external stimulus.

The sample can be an organic compound or a non-organic compound. In one aspect, the organic compound can be a biological cell or tissue.

In some embodiments, the first conformational state can be associated with a harmonic wavelength or a harmonic half-wavelength and the second conformational state can be associated with a harmonic wavelength or a harmonic half-wavelength, such that the states have different wavelengths.

The elements thus described can be applicable to each of the methods and compositions described. For example, when referring to the external stimulus as temperature, voltage, chemical, etc., such discussion is applicable to x-ray attenuating compositions as well as methods measuring x-ray attenuation of a sample or methods of enhancing x-ray attenuation of an x-ray attenuating compound, and vice versa.

It has been recognized that these x-ray attenuating compounds can provide increased contrast for use in biological as well as non-biological applications. Generally, the present compositions and methods use x-ray attenuation, which can be used in conjunction with computed tomography (CT), as CT represents the highest non-averaged temporal resolutions currently clinically available.

The attenuation of a polychromatic x-ray beam can be modulated by the distance between covalently linked strong x-ray attenuating atoms, or k-edge atoms, like iodine. Specifically, the inventors have recognized that when the interatom, such as inter-iodine, nuclear distance is closest to an integer wavelength harmonic of the energy required for photoelectric attenuation by the inner most electron orbital (K-shell), x-ray attenuation is reduced relative to when the inter-iodine nuclear distance is greater than an integer wavelength harmonic. As such, the present compositions and methods can provide enhanced x-ray attenuating compounds, including contrast agents, which are previously unknown.

Generally, x-ray attenuation can offer a unique imaging modality in that tissues are highly permeable to x-rays until the energy of the incident x-ray photon corresponds to the energy level of the inner most orbital of any atom (K-shell). At this K-edge, attenuation significantly increases and then again falls as the incident x-ray energy increases. X-ray attenuation can be described by three material parameters: the atomic number, electrons per gram, and density of the absorber. As such, the present compositions and methods can modulate x-ray attenuation by changing the molecular density of the absorber.

A novel molecule thus can be provided which changes its x-ray attenuation spectrum when the molecule is exposed to very small external stimuli, e.g., electric fields on the order of mV. As x-ray attenuation is linearly dependent on the electron density of the imaged material, this concept is utilized on the atomic scale, where the electron density of a molecule changes depending on which atom of the molecule is more likely to attenuate an x-ray photon. Specifically, iodine significantly attenuates x-rays of energy greater than 33 keV, while carbon's contribution to attenuation in the same energy range is significantly lower. It has been recognized that the distance between iodine atoms on a single molecule can modulate x-ray attenuation.

These methods and compositions allow for detailed non-invasive means for measuring biological phenomenon in three-dimensional preparations at a temporal resolution significantly closer to the time course of the excitation from the external stimulus. In other words, these compositions allow for dynamic measurements as a function of time in addition to static discrete points in time.

While monochromatic x-ray sources, and the combination of specific energy x-ray sources have long been used to increase x-ray contrast, non-specific polychromatic sources still predominate in clinical radiography. As such, it has been recognized that x-ray attenuation can be modulated by changing the density of the absorber, i.e., a molecule capable of acting as a signal transducer. The absorber or x-ray attenuating compounds can be sensitive to any number of external stimuli, including temperature, voltage, chemical, or compound. Such chemical stimuli can include ion concentration, pH, and the like. Such compound stimuli can include any compound capable of interacting with an x-ray attenuating compound. For example, a compound that binds the x-ray attenuating compound causing the x-ray attenuating compound to change from a first conformational state to a second state can be measured and/or imaged per the methods described herein. Such compounds include biological compounds such as proteins (e.g. ion channels and enzymes) and non-biological compounds such as polymers, drug delivery biopolymers, and the like.

By exploiting the unique features of these polychromatic sources and unique attenuation characteristics of large photoelectric attenuating atoms, covalently linked molecular groups can modulate overall x-ray attenuation. Furthermore, it has been recognized that this modulation is dependent on the relationship between the half-wavelength of the K-edge energy and the distance between K-shells of different atoms.

Specifically, the K-shell radius of iodine, for example, is orders of magnitude smaller than the wavelength of 33 keV (0.3758 Å) x-ray, a condition where one could assume a homogeneous wave field and thus a harmonic pseudo-oscillatory condition. The inter-iodine distance on a molecule such as diiodomethane is an order of magnitude greater (3.235 Å) than the photoionization wavelength ($\lambda_{K,I}$). Therefore, inter-iodine distance should have little to no effect on x-ray attenuation. According to that known in the art before the present invention, the probability of x-ray photon interaction should not be different between a solution containing a diiodo-alkane of specified concentration and one containing twice that concentration of a mono-iodo alkane. However, the present data provides otherwise.

As previously understood, one explanation is that the incident polychromatic x-ray results in a predomination of inelastic Compton scattering. Therefore, increasing the quantity of atoms in the phantom (density) capable of scattering x-rays will increase total attenuation. Shrimpton demonstrated that for many liquids, measured electron density quantified by Compton scatter techniques correlates well with the theoretical electron density in support of this hypothesis. (Shrimpton, Phys Med Biol 1981, 26(5)) However, compounds containing large attenuating atoms such as chlorine fell off the line of identity. This discrepancy was attributed to calibration and systematic errors. Shrimpton's observation that highly attenuating atoms do not follow the predicted line of identity is consistent with the results of the present invention that demonstrate attenuation is enhanced when a photoelectric attenuating atom is covalently linked to any other atom(s). This observation holds whether for the finding that iododecane attenuates more than a combination of iodomethane plus nonane, or the observation that diiodomethane attenuates significantly more than twice the concentration of iodomethane. Therefore, these data are inconsistent with attenuation due to the density of atoms within the entire phantom volume.

It is well established that molecular bonding modulates x-ray attenuation as demonstrated by the many different X-ray absorption fine structure (XAFS) studies using x-ray spectroscopy. However, these differences in attenuation represent small perturbations relative to the K-edge attenuation threshold. It is unclear whether the integral of total attenuation over the entire region is sufficient to observe a 10 to 20% difference in total x-ray attenuation as observed between 1,2 diiodobenzene and 1,4 diiodobenzene.

The apparent transducing effect of molecules bound to K-edge attenuating atoms may occur via a similar mechanism to that demonstrated by Xie and colleagues. In that study, they demonstrate that the material of a Young's double slit experiment can significantly impact photoelectric transmission through a double slit, by a mechanism of inductive electromagnetic fields created in the material. These data hold a possible explanation that on a molecular level, an incident photon may in fact interact with the entire molecule setting up a field which may increase the probability of photon attenuation.

An alternative explanation presently found is that the spacing between k-edge attenuating atoms modulates attenuation by a diffractive mechanism. Specifically, when atomic spacing is a wavelength harmonic of the incident photon, the integrated intensity of the diffraction pattern within the limits of the x-ray detector may fall to a local minima.

Without intending to be bound by any particular theory, the present invention provides compositions and methods for an entirely new class of conformationally active compounds for modulating x-ray attenuation that can be created for the purpose of measuring biophysical parameters such as, but certainly not limited to, membrane potential, chemical concentrations, or even possibly resolving non-crystallized protein structures using x-ray attenuating atoms instead of large fluorophores as used in fluorescence resonance energy transfer (FRET). As such, using the present techniques, existing contrast agents can be enhanced using the present methods.

EXAMPLES

The following examples illustrate embodiments of the invention that are presently known. Thus, these examples should not be considered as limitations of the present invention, but are merely in place to teach how to make the useful compositions of the present invention based upon current experimental data.

Example 1

The phantom consisted of two aluminum plates with 4 equally spaced wells of 2 cm diameter and 1 cm depth compressing a glass microscope slide (Corning Glass Works, Corning, N.Y.) as seen in FIG. 1. Leak between the top compressing aluminum plate and the cover slip was prevented by the inclusion of a neoprene O-ring. Each well was filled with 2 ml of solution for imaging such that the x-ray path length in each well was constant.

Solutions

The following substances were dissolved in 10 ml of dimethyl sulfoxide (DMSO) and then aliquotted into 2 ml of solution per well: Iodomethane (100, 150, 300, and 450 mM), iododecane (100 mM), nonane (100 mM), diiodomethane (150 mM), 1,2-diiodobenzene (150 mM), 1,3-diiodobenzene (150 mM), 1,4-diiodobenzene (150 mM), and 2,6-diiodo-4-nitroanaline (150 mM). All compounds were >98% pure and obtained from Sigma-Aldrich.

Absorbance

Absorbance (directly correlated to attenuation) was measured with an OEC Compact 7600 fluoroscope. The peak applied tube voltage (tube voltage) was 42 kVp (±10% according to manufacturer). Beam quality is listed in Table 1.

TABLE 1

| Beam quality. | | |
|---|---|---|
| kV | HVL (mm Al) | Effective energy |
| 36 | 2.1 | 30.8 |
| 38 | 2.2 | 31.7 |
| 40 | 2.5 | 33.4 |
| 42 | 2.6 | 33.5 |
| 44 | 2.8 | 34.5 |
| 46 | 2.9 | 35.3 |
| 48 | 3.1 | 36.0 |

Current was 0.5 mA (±10% according to manufacturer), and all samples were exposed for 0.5 seconds. The fluoroscope was in full manual mode. Tube voltage was varied to determine the relationship between absorbance and x-ray energy. The output of the fluoroscope was connected via BNC to a National Instruments data acquisition card. Fifty frames were acquired and temporally averaged using custom software written in Matlab (Mathworks, Natick, Mass.) to quantify absorbance per well. Absorbance (A) for each liquid sample (As) was estimated by a modified Beer-Lambert equation:

$$A_n = -\log_{10}\left(\frac{I_{S,n}}{I_{E,n}}\right) \quad (1)$$

The value n indicates the well number as shown in FIG. 1. Is corresponds to the grayscale image intensity of the sample. $I_E$ corresponds to the grayscale intensity of the empty well which we equate with the intensity of the incident light that reaches the detector.

Density

One milliliter of each solution was weighed in a Mettler Toledo AL54 precision balance scale in order to determine the density in g/ml (n=16 for each compound). Theoretical density for liquid compounds was estimated by the following equation:

$$d_S = \frac{[V_u * d_u + (1000 - V_u) * d_v]}{1000} \quad (2)$$

where $V_u$=Solute Volume, $d_u$=Solute density, and $d_v$=Solvent density.

Molecular Dynamics

Chemsketch (Advanced Chemistry Development, Inc. Toronto, Ontario) was used to energetically optimize all molecules. Molecular mechanics with force fields are based on CHARMM parameterization. Inter-iodine distance ($d_I$) was quantified from iodine nucleus to nucleus. The harmonic error ($E_H$) is quantified as the fractional remainder of the inter-atom distance (d) and the wavelength of the photon necessary for K-shell photoelectric attenuation ($\lambda_K$). For iodine, the interatom distance is $d_{I,I}$, and the wavelength for K-shell photoelectric attenuation ($\lambda_{K,I}$) is 0.375 Å.

$$E_H = \frac{d_{l,I}}{\lambda_{K,I}} - \left\lfloor \frac{d_{l,I}}{\lambda_{K,I}} \right\rfloor \quad (3)$$

$\lfloor \: \rfloor$ is the floor function. $E_H$ is bounded from 0 to 1 for all elements.

Statistics

The four wells per phantom were averaged to yield the average absorbance for a particular experiment. Each experiment was repeated (n=6, unless otherwise noted). Significance between two measurements was quantified by unpaired, 2-tailed Student's t-tests assuming equal variance. A p<0.01 was considered statistically significant. All composite measurements are presented as mean±S.E.M.

A linear model for attenuation as a function of density and harmonic error ($E_H$) with beam energy as a factor was fit using the statistical package R (The R Foundation, Vienna Austria).

Results

Validation

Figure 1:
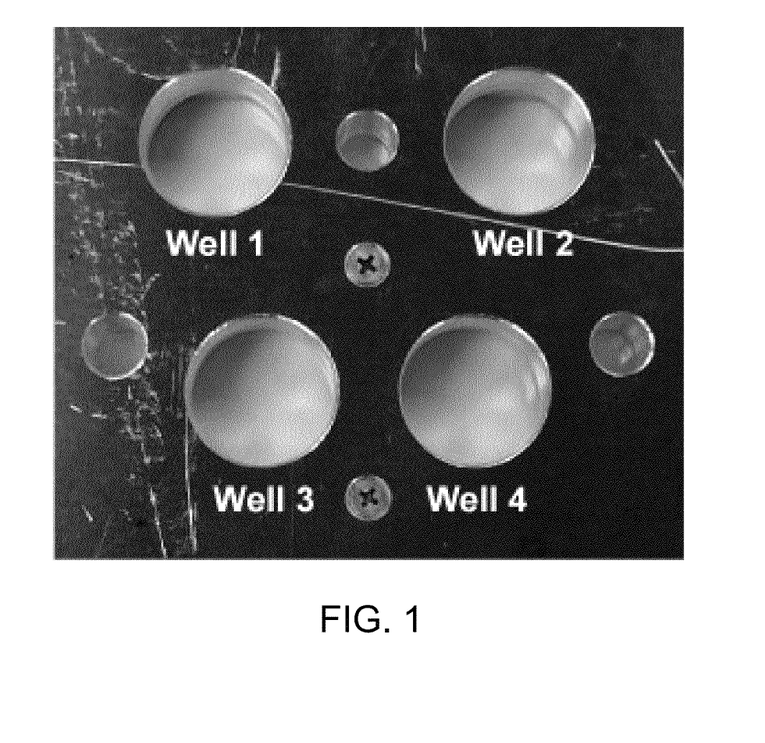
FIG. 1 is a photograph of the aluminum phantom having four large wells capable of holding 2 ml samples of solution with three smaller empty wells used for calibration.
Figure 2A:
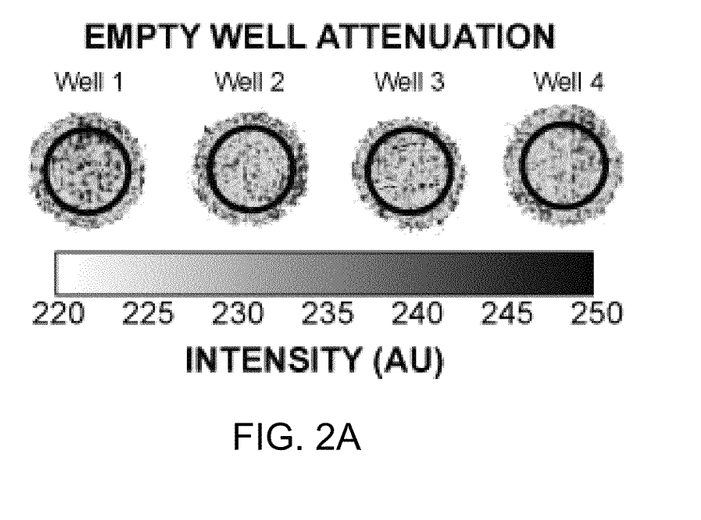
FIG. 2(A) provides attenuation data from the four wells represented by discrete grayscale plots, with a grayscale attenuation bar defining the grayscale, showing unequal attenuation properties per well.
Figure 2B:
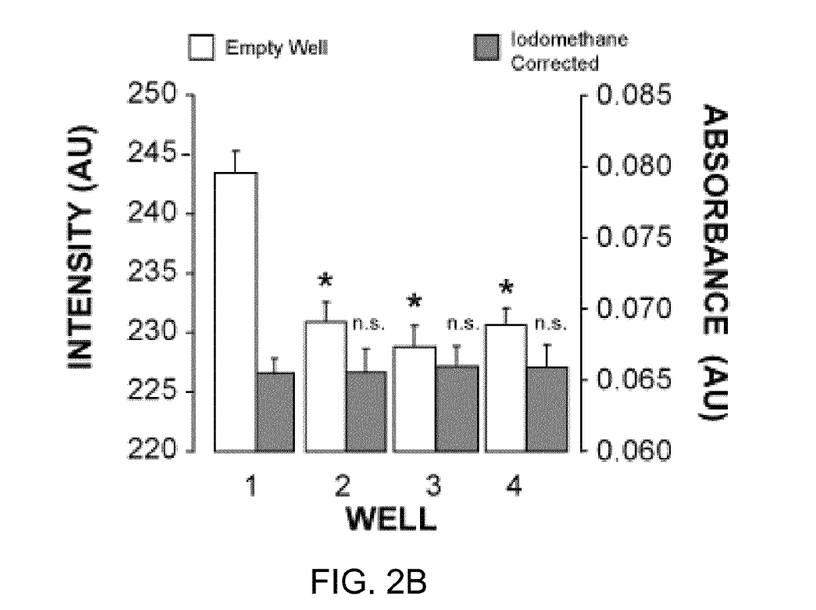
FIG. 2(B) demonstrates that empty wells 2, 3 and 4 (white bars) have significantly higher attenuation values than well 1 (*, $p<0.01$). After calculating absorbance using Beer-Lambert's law, there were no significant absorbance differences of iodomethane between wells (gray bars). C.

Since the fluoroscope emits a polychromatic conical beam, it was important to determine inter-well variability. Raw uncorrected images of the phantom in FIG. 2A demonstrate relative x-ray transmitted intensity ($I_B$) heterogeneity within and between empty wells due to a 42 kVp tube voltage. X-ray intensity was lowest in Well 1 as evidenced by the greater number of dark pixel relative to all other wells. Maximal difference between wells was on the order of 30 arbitrary absorbance units (A.U.) as illustrated by the color bar range in FIG. 2A. The edges of each well appear to have larger absorbance values than the center of the well, which may be due to the concave meniscus of the solution. Therefore to minimize edge effects, the black circle in each well of FIG. 2A indicates the region of interest (ROI) from which absorbance was measured. ROI area was constant for all wells, and total x-ray absorbance was quantified as the average absorbance within the ROI. The average intensity for empty wells 2, 3 and 4 (n=46) were significantly different relative to well 1 (*, p<0.01). After calculating absorbance (eqn. 1) for 150 mM iodomethane, there were no significant differences between wells (FIG. 2B, gray bars, no significance relative to well 1).

Figure 2C:
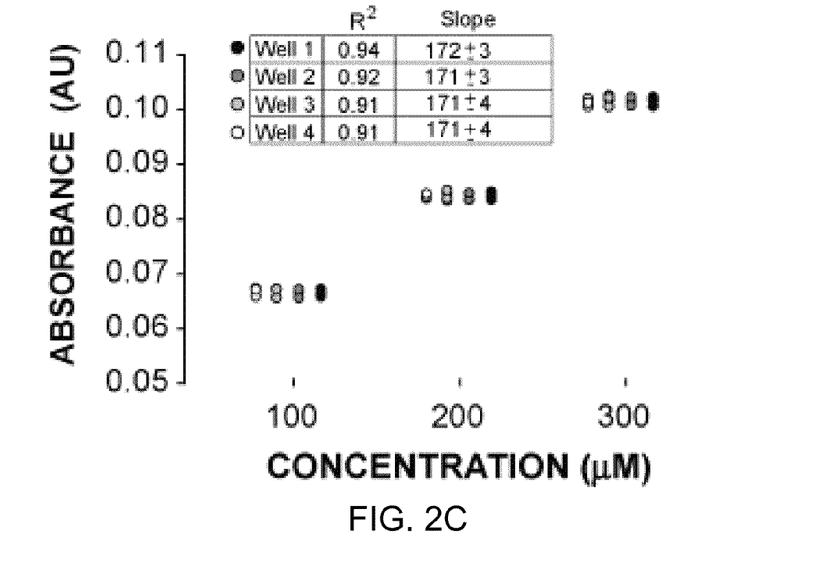
FIG. 2(C) provides an attenuation vs. concentration plot after normalization, showing that attenuation for each well increased linearly as the concentration of iodomethane was increased. The inset provides the linear fit parameters, demonstrating that there was no significant difference between wells.

Likewise, increasing concentrations of iodomethane increased absorbance in a linear fashion for all wells as demonstrated in FIG. 2C (n=5, per concentration). The four wells were separated from each other on the x-axis for the purpose of visualization, and this had no effect on the calculated slope. For each well, the correlation coefficient was greater than 0.9 and slopes were not significantly different (FIG. 2C, Table Insert).

Iodine and Alkanes

Figure 3A:
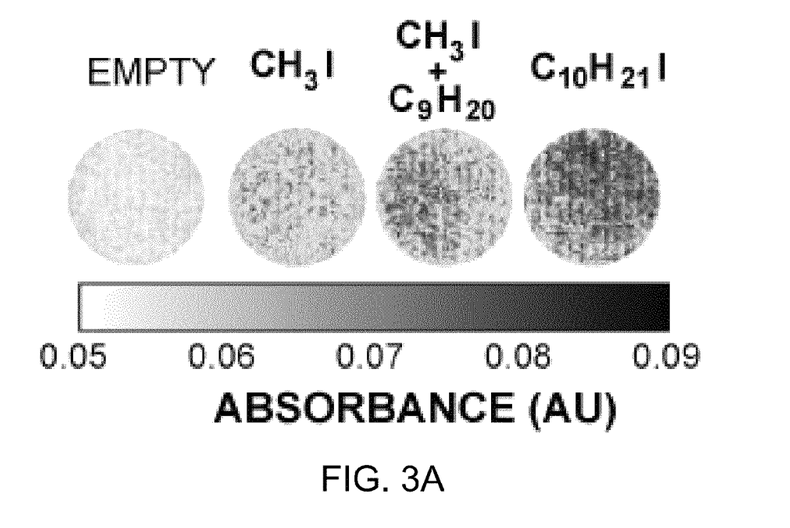
FIGS. 3A and 3B shows density and the mixture rule do not always explain absorbance differences. A. Representative absorbance of iodomethane ($CH_3I$), iodomethane and nonane ($CH_3I+C_9H_{20}$), and iododecane ($C_{10}H_{21}I$). B. Summary data demonstrates that iododecane absorbs significantly more than iodomethane and nonane (#). Iododecane and iodomethane+nonane both attenuate significantly more than iodomethane alone (*). However, iodomethane is denser than iodomethane+nonane and iododecane (Table).
Figure 3B:
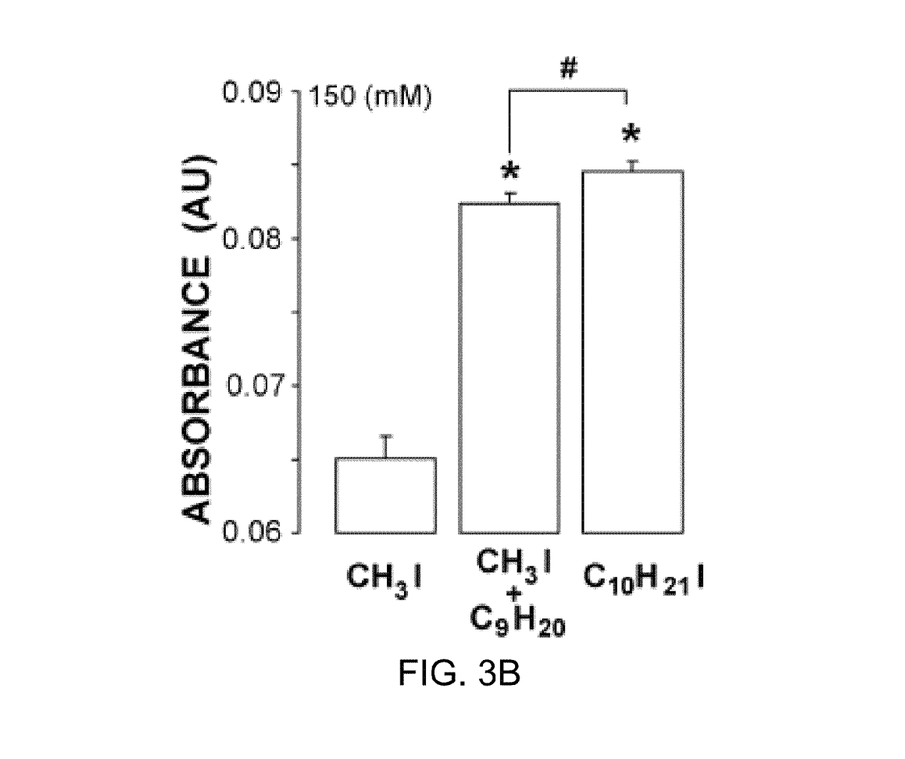

Equimolar iodomethane ($CH_3I$) absorbance (42 kVp tube voltage) without and with nonane ($C_9H_{20}$, 100 mM) was compared to 100 mM iodododecane ($C_{10}H_{21}I$) absorbance in FIG. 3. Iodomethane+nonane ($CH_3I+C_9H_{20}$) have an equal number of iodine and carbon atoms relative to iodododecane, but iodododecane has two fewer hydrogen atoms. Representative data in FIG. 3A demonstrates that iodomethane (150 mM) absorbs less than iodomethane (150 mM)+nonane (150 mM). Covalently bonded nonane to iodomethane, to make iodododecane (150 mM), increases absorbance above iodomethane and iodomethane+nonane. Summary data from all experiments in FIG. 3B demonstrates that iodomethane+nonane and iodododecane absorb significantly more than iodomethane alone by 12% and 22% respectively. Additionally, iodododecane absorbs significantly more than iodomethane+nonane by 9%. Both theoretical and experimentally measured iodomethane solution density is significantly greater than both iodomethane+nonane and iodododecane solution density as demonstrated in Table 2.

TABLE 2

Solution density for all compounds dissolved in 1 ml DMSO.

| | Estimated Density (g/ml) | Experimental Density (g/ml) |
|---|---|---|
| Iodomethane (150 mM) | 1.1121 | 1.1119 ± 0.0021 |
| Iodomethane (300 mM) | 1.1158 | 1.1128 ± 0.0019 |
| Iodomethane + Nonane | 1.1013 | 1.1009 ± 0.0015 |
| Iodododecane | 1.1059 | 1.1055 ± 0.0012 |
| Diiodomethane | 1.1281 | 1.1241 ± 0.0011 |
| 1,2 Diiodobenzene | 1.1295 | 1.1219 ± 0.0008 |
| 1,3 Diiodobenzene | N/A | 1.1262 ± 0.0021 |
| 1,4 Diiodobenzene | N/A | 1.1239 ± 0.0009 |
| 2,6-Diiodo-4-Nitroanaline | N/A | 1.1281 ± 0.0023 |

* p < 0.05 vs. all other densities

Solution density for all compounds dissolved in DMSO were estimated when the compound was liquid at room temperature.

Iodomethane vs. Diiodomethane

Figure 4A:
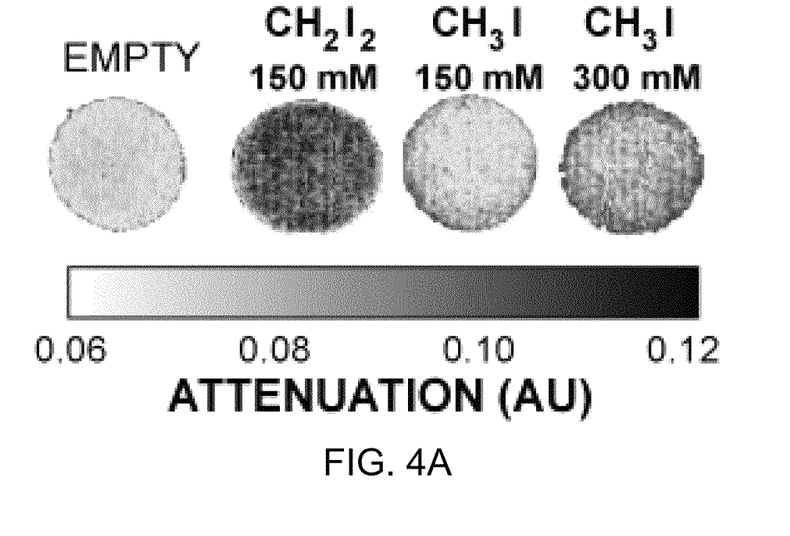
FIG. 4A is a representative absorbance of diiodomethane, iodomethane, and twice the concentration of iodomethane (300 mM).

Representative absorbance of an empty well, a well with 150 mM diiodomethane ($CH_2I_2$), 150 mM iodomethane ($CH_3I$), and 300 mM iodomethane are shown in FIG. 4A (42 kVp tube voltage). The empty well is provided for reference and to demonstrate the degree of contrast between samples. Absorbance due to diiodomethane ($CH_2I_2$) was greater than absorbance due to equimolar iodomethane as expected. This is summarized in FIG. 4B (*, p<0.01, n=16 for all compounds).

Figure 4B:
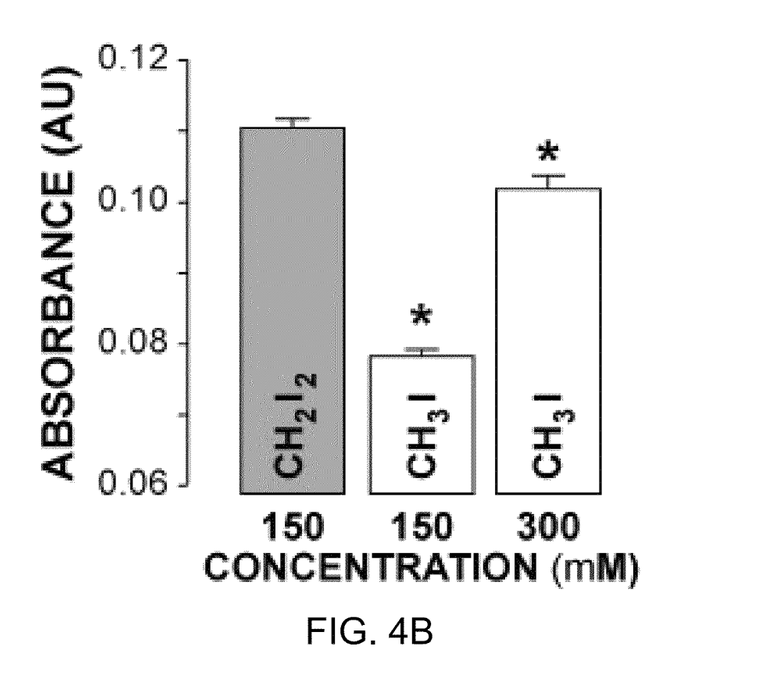
In FIG. 4B summary data demonstrates that 150 mM iodomethane and 300 mM iodomethane attenuate significantly less than diiodomethane (*).

Representative and summary data in FIG. 4 demonstrates that twice the concentration of iodomethane (2× iodomethane, 300 mM) absorbs significantly less than diiodomethane (1× diiodomethane, 150 mM). The number of iodine atoms is equal in both solutions. For all experiments, 1× Diiodomethane (100 m) absorbed significantly more than 2× iodomethane (FIG. 4B). The densities of the 1× and 2× iodomethane solutions (estimated and measured in Table 2) are less than diiodomethane.

Figure 5:
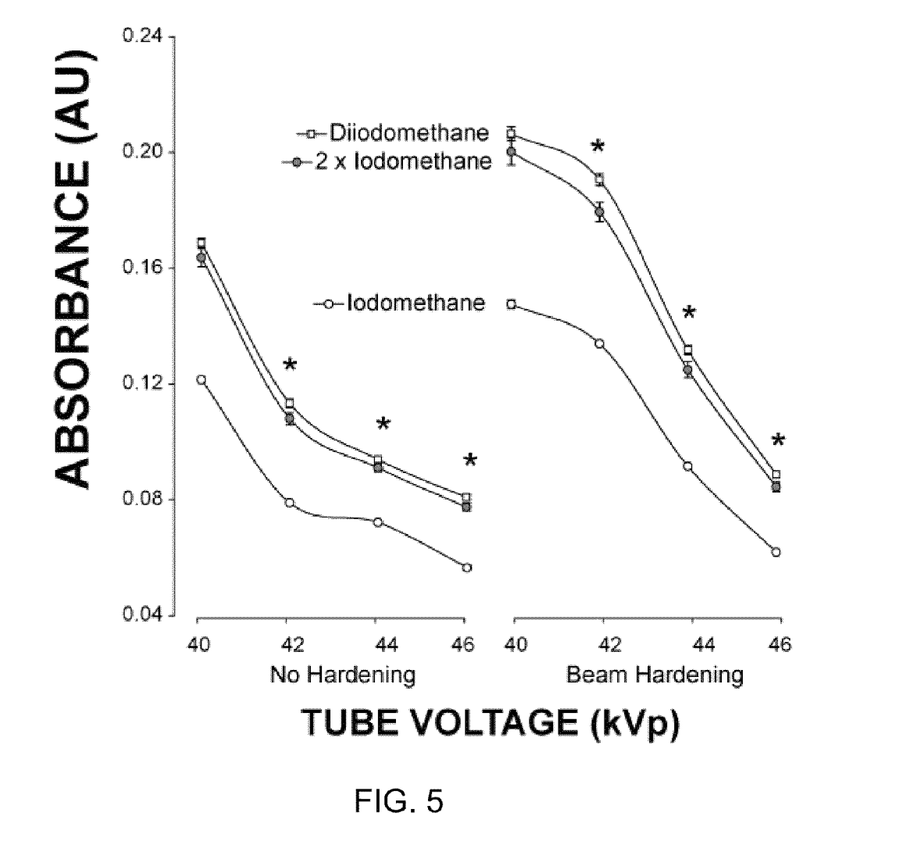
FIG. 5 is a graph of absorbance versus tube voltage. Increasing x-ray energy decreases absorbance, and beam hardening increases absorbance. Diiodomethane (150 mM) absorbs significantly more than equal molar iodomethane (Iodomethane) and twice the concentration of iodomethane (2×Iodomethane) at tube voltages of 42, 44, and 46 (*, $p<0.01$). With beam hardening, the same is true. Additionally, beam hardening significantly increases absorbance by all three samples. The relative absorbance differences between 150 mM diiodomethane, 150 mM iodomethane and 300 mM iodomethane decrease as tube voltage increases.

Experiments were repeated with the fluoroscope set to a voltage of 40, 42, 44, and 46 kVp with and without the use of a 3 mm thick aluminum plate placed on the beam output to harden the beam. Summary data in FIG. 5 demonstrates that for both unfiltered and hardened beams, x-ray absorbance for iodomethane (both concentrations) and diiodomethane compounds significantly decreased with increasing energy. Diiodomethane absorbed significantly more (*, p<0.01) than iodomethane and 2× iodomethane for all tube voltages, consistent with results at 42 kVp.

Beam hardening increased absorbance for all samples and the separation between diiodomethane and 2× iodomethane at 42 and 44 kVp. This difference was attenuated at higher tube voltages. Specifically, the difference between diiodomethane and 2× iodomethane absorbance measured at a tube voltage of 42 kVp was significantly greater than the difference between the two substances at either 44 or 46 kVp tube voltages (0.010±0.002 [42 kVp], 0.005±0.001 [44 kVp] and 0.002±0.001 [46 kVp]).

Diiodo-Aromatic Rings

Absorbance was quantified for 2,6-diiodo-4-nitroanaline and three positional isomers of diiodobenzene ($C_6H_4I_2$) (1,2 diiodobenzene, 1,3 diiodobenzene, and 1,4 diiodobenzene). The diiodobenzenes were chosen because, like diiodomethane, the iodine atoms are at fixed distances from each other. Furthermore, the diiodobenzenes have identical chemical formulae removing the confounding influence of electrons per gram of solute. The compound 2,6-diiodo-4-nitroanaline also has iodine atoms at fixed distances from each other and an additional electron withdrawing nitro group that modulates the inter-iodine distance.

Figure 6A:
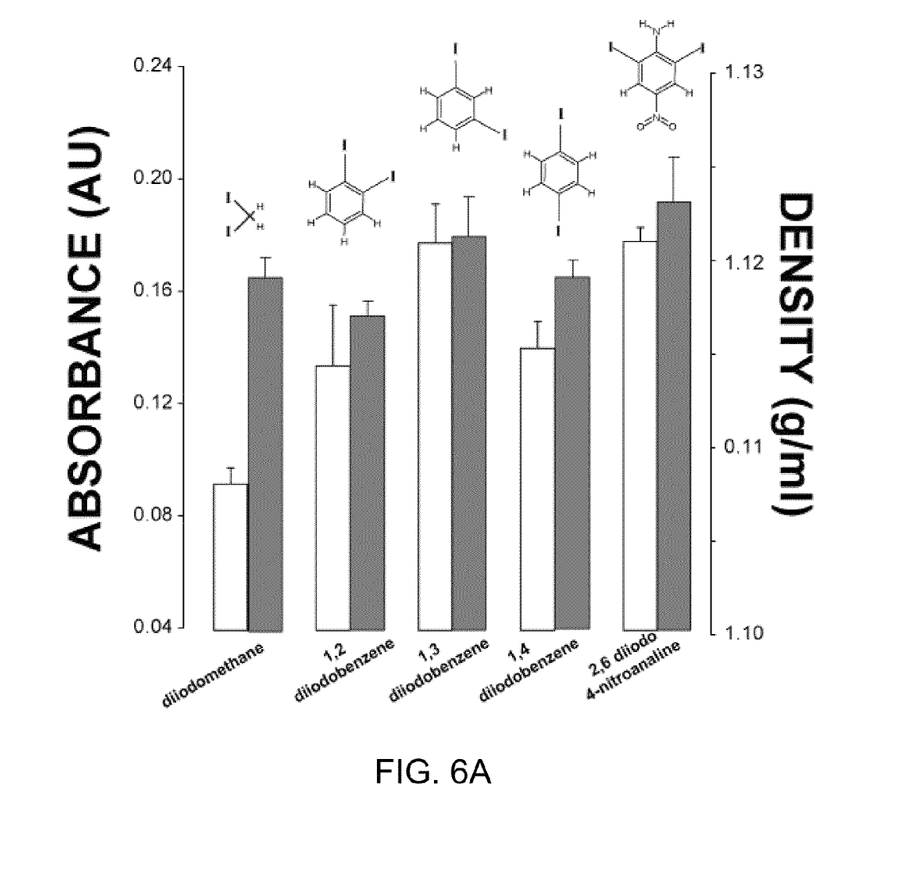
FIG. 6A is a bar graph of absorbance and density for several diiodo compounds. Absorbance correlates with the harmonic error at low energies and density at high energies. The molecular sketch of each compound is shown above the relative absorbance and measured density of each compound. 1,3 diiodobenzene and 2,6 diiodo-4-nitroanaline attenuate significantly more ($p<0.01$) than other compounds. Diiodomethane absorbs significantly less ($p<0.01$) than all other compounds.

FIG. 6A presents absorbance of all compounds with beam hardening at a tube voltage of 42 kVp (white bars). Diiodomethane absorbs significantly less than all other compounds, while 1,3 diiodobenzene and 2,6-diiodo-4-nitroanaline attenuate significantly more than all other compounds. Additionally, 2,6-diiodo-4-nitroanaline does not attenuate significantly more than 1,3 diiodobenzene.

Figure 6B:
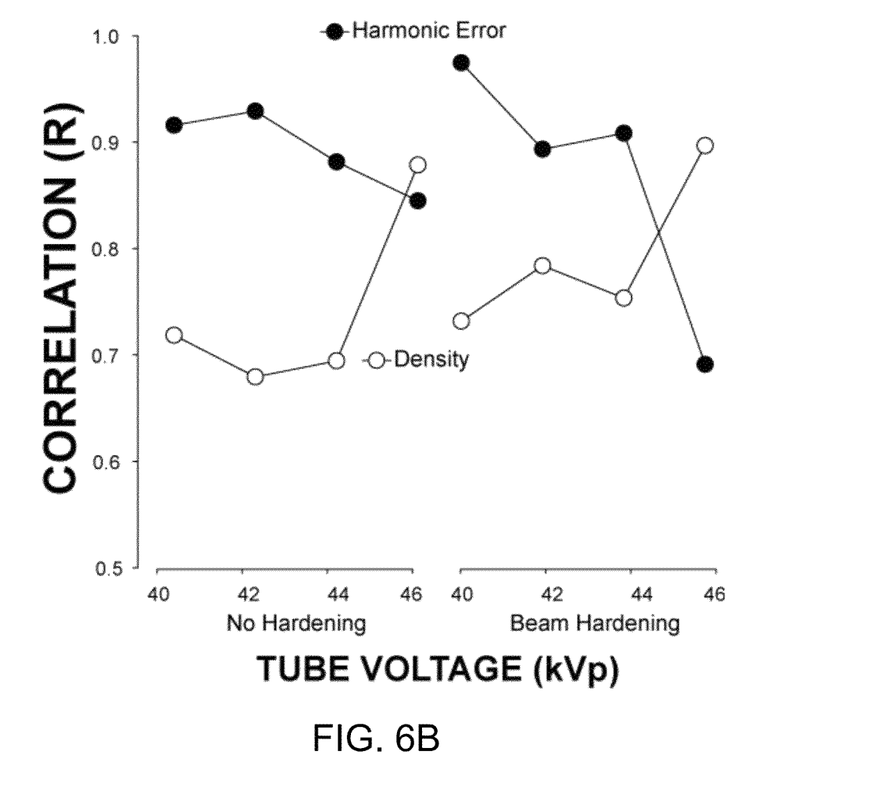
FIG. 6B is a graph of correlation (R) versus tube voltage. Absorbance of each compound was correlated to either the experimental density (white circles) or the harmonic error (black circles). The correlation coefficient is plotted as a function of peak tube voltage with and without beam hardening.

The density for each compound in DMSO is listed in Table 2. The experimentally measured density of each compound is graphed in FIG. 6 (gray bars) next to absorbance for visual comparison. There were no significant empirical differences in density between compounds. However, 2,6-diiodo-4-nitroanaline trended towards a significantly greater density than all other compounds (p<0.11). FIG. 6B (open circles) demonstrates that the correlation coefficient between absorbance and density increases with increasing tube voltage. This relationship did not achieve significance until the tube voltage was 46 kVp.

Conversely, the correlation between absorbance and harmonic error, defined by equation 3, was higher than the correlation between absorbance and density for low x-ray energies. The absorbance and harmonic error correlation dropped as energy increased for both the unfiltered and hardened beam. This relationship was significant for all tube voltages.

Discussion

While mono-chromatic x-ray sources, and the combination of specific energy x-ray sources have long been used to increase x-ray contrast, non-specific polychromatic sources still predominate in clinical radiography. Therefore, x-ray absorbance can be modulated, in part, by the distance between K-edge attenuating atoms like iodine.

Mixture Rule

The mixture rule suggests that the mass attenuation coefficient of a material is the weighted sum of the mass attenuation coefficients of its constitutive elements. The mixture rule is consistent with the observation that iodomethane+nonane attenuates significantly more than iodomethane alone. However it cannot explain the difference observed between iodododecane and iodomethane+nonane. Both solutions have equal numbers of iodine and carbon atoms.

Furthermore, the observation that diiodomethane absorbs significantly more than 2×iodomethane is inconsistent with the mixture rule which would predict that 2× iodomethane should absorb equal to or greater than diiodomethane. Iodomethane (2×) has twice as many carbons and hydrogen atoms as diiodomethane. Additionally, the number of electrons per gram is significantly higher in the 2× iodomethane phantom than 1× diiodomethane.

The mixture rule also does not explain the apparent differences in x-ray absorbance between the structurally isomeric diiodobenzene molecules. For example, 1,3 diiodobenzene absorbed significantly more than 1,2 diiodobenze and 1,4 diiodobenzene. All three compounds have identical molecular formulae. Likewise, 2,6-diiodo-4-nitroanaline did not attenuate significantly more than 1,3 diiodobenzene despite the additional three nitrogen and two oxygen atoms. Importantly, carbon, nitrogen, and oxygen should not contribute significantly to x-ray absorbance due to x-ray photons produced by the 42 kV tube voltage.

These findings are consistent with previous studies which have demonstrated that the mixture rule can well approximate mass absorbance of biological samples, but it is not well suited for determining the mass attenuation coefficient of compounds. One explanation could be that density or the inter-atomic distances play a role in x-ray absorbance.

Density

Absorbance of iodomethane, iodomethane+nonane, and iododecane solutions are inconsistent with the observed absorbance differences attributable to density. Iodomethane+nonane absorbance is significantly higher than iodomethane alone despite decreased iodomethane+nonane density (theoretical and experimental). It could be argued that this effect is simply due to a greater number of carbon atoms provided by the nonane (electrons per gram), which increases scattering events in this energy range. This particular interpretation does not agree with the observation that iododecane, a molecule that has equal number of carbon and iodine atoms as the iodomethane+nonane solution, absorbs significantly more than iodomethane and iodomethane+nonane. Additionally, iododecane solution density was significantly lower than iodomethane. There was no significant difference in experimentally measured density between iododecane and iodomethane+nonane. Therefore, large photoelectric attenuating atoms covalently linked to non-K-edge attenuating groups appear to increase absorbance.

On the other hand, the difference in absorbance could potentially be explained by differences in density between 2× iodomethane and diiodomethane as shown in Table 2. However, this interpretation is confounded by the inability to detect absorbance differences between the two samples at high tube voltages. At higher x-ray energies, the number of x-ray dependent interaction should decrease as observed. However, the relative contribution of photon scattering events, dependent on material density, should conversely increase. Likewise, there was no significant absorbance difference between the samples at low tube voltages (40 kVp). The predominant difference between the two samples occurred when tube voltage was between 42 and 44 kVp. Therefore, these tube voltages (42-44 kVp) were high enough to produce significantly more photons with energies near the iodine K-shell energy (33 keV, see Table 1) for photoelectric interaction with iodine atoms. Further, the difference in x-ray absorbance between the two samples indicates that the principal attenuating mechanism may be photoelectric in nature.

The diiodobenzene results are also incongruous with the hypothesis that absorbance differences are solely attributable to density differences. As mentioned previously, absorbance should increase with the density of a compound. Correlation between absorbance and density is relatively weak for diiodomethane, 1,2 diiodobenzene, 1,3 diiodobenzene, 1,4-diiodobenzene and 2,6-diiodo-4-nitroanaline at low tube voltages with and without beam hardening (R=0.65).

However, the correlation between absorbance and density should increase as photon energy is increased. In these experiments, the correlation between absorbance and density did increase as energy increased which is consistent with the relationship between absorbance and density (FIG. 6). Therefore, a significant difference in density between diiodomethane and the diiodobenzene compounds was not measured, x-ray absorbance measurements may have been able to detect density differences based on absorbance. The density of 2,6-diiodo-4-nitroanaline trended towards significance with respect to the other experimental compounds. However, absorbance was not significantly different from 1,3 diiodobenzene, for example, for any energy. Therefore, these data indicate that absorbance and density follow a predictable relationship when x-ray energy is farther away from the K-edge energy of iodine, for example. However, the density does not well explain difference in absorbance near the iodine K-edge energy.

Harmonic Error

At low tube voltages, x-ray absorbance correlated better with the harmonic error than it did with density (R>0.9). Beam hardening further increased correlation at low tube energies near the iodine K-edge energy. This indicates that the distance between iodine atoms relative to the K-shell energy affects photoelectric absorbance, and the differential absorbance observed between compounds is not simply a function of the solution density.

It is assumed that the radius of the K-shell is relevant for the photoionization process. For iodine, the k-edge radius can be estimated by the Hartree approximation of $r_K = a_0/(Z-2)$, where $a_0$ is the k-shell Bohr radius (0.5 Å), and Z is the atomic number of iodine (53). Hartree's approximation yields a K-shell radius for iodine of $0.98 \times 10^{-2}$ Å, which is orders of magnitude smaller than the wavelength of a 33 keV ($\lambda_{K,I}$=0.3758 Å) x-ray photon. This is a condition where one could assume a homogeneous wave field and thus a harmonic pseudo-oscillatory condition. The inter-iodine distance on a molecule such as diiodomethane is an order of magnitude greater (3.235 Å) than the iodine photoionizating wavelength ($\lambda_{K,I}$). Therefore, inter-iodine distance should have little to no effect on x-ray absorbance.

Shrimpton demonstrated that for many liquids, measured electron density quantified by Compton scattering techniques correlates well with the theoretical electron density. Compounds containing large attenuating atoms such as chlorine fell off the line of identity. This discrepancy was attributed to calibration and systematic errors. However, Shrimpton's observation that highly attenuating atoms do not follow the predicted line of identity is consistent with the results of this invention that demonstrate absorbance is enhanced when a photoelectric attenuating atom is covalently linked to any other atom(s). This observation holds for both the finding that iododecane absorbs more than a combination of iodomethane+nonane and that diiodomethane absorbs significantly more than twice the concentration of iodomethane.

Mechanisms

Molecular bonding modulates x-ray absorbance as demonstrated by the many different X-ray absorption fine structure (XAFS) studies using x-ray spectroscopy. However, these differences in absorbance represent relatively small perturbations relative to the K-edge absorbance threshold. It is unclear whether the integral of total absorbance over the entire region is sufficient to observe a 10 to 20% difference in total x-ray absorbance as observed between 1,2 diiodobenzene and 1,3 diiodobenzene for example. Further studies are needed to address this potential mechanism.

The apparent photon translating effect of molecules bound to K-edge attenuating atoms may occur via a mechanism demonstrated as follows. The material of a Young's double slit experiment can significantly impact photoelectric transmission through a double slit by a mechanism of inductive electromagnetic fields created in the material. These data may indicate that on a molecular level, an incident photon may in fact interact with the entire molecule setting up a field which may increase the probability of photon absorbance. One difficulty with this interpretation is that the carbon atoms between iodine atoms have relatively low conductivities.

An alternative explanation is that the spacing between k-edge attenuating atoms modulates absorbance by a diffractive mechanism. Specifically, when atomic spacing is a wavelength harmonic of the incident photon, the integrated intensity of the diffraction pattern within the limits of the x-ray detector may fall to a local minimum.

Lastly, the interaction could be consistent with the Copenhagen Interpretation of Young's double slit experiment, which indicates that a photon interacts with both slits but does not spatially resolve until it is measured. In these experiments, the openings, or slits, of Young's double slit experiment correspond to strong photoelectrically attenuating atoms, and the obstacle in the double slit experiment is electromagnetically transparent matter. In effect, there is a double obstacle rather than double slit experiment.

Regardless of the mechanism by which absorbance increases in these compounds, this invention raises an entire new class of conformationally active compounds for modulating x-ray absorbance for the purpose of measuring biophysical parameters such as, but certainly not limited to, membrane potential, chemical concentrations, or resolving non-crystallized protein structures using x-ray attenuating atoms instead of large fluorophores as used in Förster resonance energy transfer (FRET). This can be done by making molecules that vary the distance between strong K-edge attenuating atoms in response to external stimuli.

Limitations

These examples utilized a polychromatic x-ray beam from a fluoroscope instead of monochromatic photons capable of further elucidating the direct mechanism by which absorbance occurs. However, this limitation does not detract from the finding that x-ray absorbance in molecules with multiple K-edge attenuating atoms is greatest when the distance between those atoms is greater than a harmonic of the K-edge energy.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A method of measuring x-ray attenuation of a sample with an x-ray attenuating compound, comprising
   a) adding the x-ray attenuating compound to the sample, the sample having an external stimulus in an amount sufficient to modulate the x-ray attenuating compound from a first conformational state to a second conformational state;
   b) exposing the x-ray attenuating compound to an energy source; and
   c) calculating the amount of the external stimulus present in the sample by measuring a difference in x-ray attenuation of the energy source provided by the first conformational state and the second conformational state of the x-ray attenuating molecule,
   wherein the x-ray attenuating compound, comprises:
   a molecule having at least two conformational states;
   a first k-edge atom attached to the molecule at a first position, wherein the first k-edge atom is iodine; and
   a second k-edge atom attached to the molecule at a second position, wherein the molecule changes from a first conformational state to a second conformational state in response to an external stimulus, wherein a first interatom distance between the first k-edge atom and the second k-edge atom in the first conformational state is within a first harmonic error of 0 to about 0.2, and wherein a second interatom distance between the first k-edge atom and the second k-edge atom in the second conformational state is within a second harmonic error with a remainder of about 0.8 to 0.99.

2. The method of claim 1, further comprising the steps of collecting data of the external stimulus and imaging the data.

3. The method of claim 2, wherein the step of collecting and imaging are dynamic.

4. The method of claim 1, wherein the exposing includes use of a computed tomography (CT) instrumentation.

5. The method of claim 1, wherein the molecule is an organic molecule.

6. The method of claim 5, wherein the organic molecule is a substituted or unsubstituted, aliphatic and/or aromatic, carbon molecule.

7. The method of claim 1, wherein the first k-edge atom and the second k-edge atom are both iodine.

8. The method of claim 1, wherein the first harmonic error is 0 to about 0.1.

9. The method of claim 1, wherein the second harmonic error is about 0.9 to 0.99.

10. The method of claim 1, wherein the external stimulus is temperature.

11. The method of claim 1, wherein the external stimulus is voltage, chemical, or a compound.

12. The method of claim 1, further comprising a third k-edge atom and a fourth k-edge atom, wherein a third interatom distance between the third k-edge atom and the fourth k-edge atom in the first conformational is within a third harmonic error of within about 0.2 of 0 or 1, and wherein a fourth interatom distance between the third k-edge atom and the fourth k-edge atom in the second conformational state is within a fourth harmonic error of within about 0.2 of 0 or 1.

* * * * *